United States Patent [19]

Sanderson et al.

[11] Patent Number: 5,354,925
[45] Date of Patent: Oct. 11, 1994

[54] USE OF SUPPORTED LEAD OXIDE CATALYST IN THE PREPARATION OF TERTIARY BUTYL ALCOHOL FROM TERTIARY BUTYL HYDROPEROXIDE

[75] Inventors: John R. Sanderson, Leander; Roger G. Duranleau, Georgetown, both of Tex.

[73] Assignee: Texaco Chemical Company, White Plains, N.Y.

[21] Appl. No.: 150,920

[22] Filed: Nov. 12, 1993

[51] Int. Cl.$^5$ .................... C07C 29/132; C07C 31/12
[52] U.S. Cl. ................ 568/909.8; 568/385; 568/561
[58] Field of Search ..................... 568/909.8

[56] References Cited

FOREIGN PATENT DOCUMENTS 1417105  10/1965  France ...................... 568/909.8

*Primary Examiner*—Joseph E. Evans
*Attorney, Agent, or Firm*—James L. Bailey; Kenneth R. Priem; Carl G. Ries

[57] ABSTRACT

A method for preparing tertiary butyl alcohol wherein a feedstock comprising a solvent solution of tertiary butyl hydroperoxide in tertiary butyl alcohol or a mixture of tertiary butyl alcohol with isobutane is charged to a hydroperoxide decomposition reaction zone containing a catalytically effective amount of a hydroperoxide decomposition catalyst consisting essentially of lead oxide supported on alumina and is brought into contact with the catalyst in liquid phase with agitation under hydroperoxide decomposition reaction conditions to convert the tertiary butyl hydroperoxide to decomposition products, principally tertiary butyl alcohol.

7 Claims, No Drawings

USE OF SUPPORTED LEAD OXIDE CATALYST IN THE PREPARATION OF TERTIARY BUTYL ALCOHOL FROM TERTIARY BUTYL HYDROPEROXIDE

BACKGROUND OF THE INVENTION

1. Field of the Invention

This invention relates to the catalytic decomposition of tertiary butyl hydroperoxide (TBHP). More particularly, this invention relates to a method for the preparation of tertiary butyl alcohol (TBA) by the catalytic decomposition of tertiary butyl hydroperoxide. Still more particularly, this invention relates to a method wherein an alumina supported lead oxide catalyst is used to catalyze the substantially selective decomposition of tertiary butyl hydroperoxide to tertiary butyl alcohol.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide to form tertiary butyl alcohol.

In the text entitled "Organic Peroxides" edited by Daniel Swern (Wiley Interscience, a Division of John Wiley & Sons, New York), in Vol. II on page 157 it is stated that the metal-ion-catalyzed decomposition of primary hydroperoxides yields mainly alcohols, aldehydes and carboxylic acids, citing as an example the decomposition of hydroxymethylhydroperoxide with aqueous ferrous sulfate to provide formaldehyde, formic acid and water.

Quin U.S. Pat. No. 2,854,487 discloses the hydrogenation of hydrocarbon peroxides in the presence of hydrogen and palladium on activated alumina to provide carbinols.

In Massie U.S. Pat. No. 3,775,472 a process is disclosed wherein alkyl substituted aromatic hydrocarbons are oxidized to products such as aromatic alcohols, aldehydes and carboxylic acids in the presence of ruthenium compounds.

Grane U.S. Pat. No. 3,474,151 discloses that tertiary butyl alcohol starts to dehydrate at 450° F. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes.

Grane et al. U.S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 475° for about 1 to 10 minutes. Heating tertiary butyl alcohol containing small amounts of peroxides at high temperatures for even short periods of time to remove the peroxides produces undesirable products such as isobutylene.

Grane et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig. in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decomposed by "hot aging" at 250°–350° F. at a pressure lower than the pressure in the oxidation zone. The tertiary butyl alcohol can be further subjected to a cleanup treatment at 375°–475° F. for 1 to 10 minutes. Worrell et al. in U.S. Pat. No. 4,296,263 disclose a related process wherein the feedstock is a mixture of normal butane with isobutane and wherein the oxidation catalyst is a soluble form of chromium, cobalt, nickel, manganese, molybdenum, or a mixture thereof.

In U.S. Pat. No. 3,505,360, Allison et al. disclose a method wherein an alkenyl hydroperoxide is decomposed in the presence of a catalyst based on a compound of a Group IV-A, V-A or VI-A metal. Taylor et al., in U.S. Pat. No. 4,508,923 disclose the use of a catalyst system comprising ruthenium and chromium for decomposing organic hydroperoxides. The use of a cobalt borate catalyst for the decomposition of hydroperoxides is disclosed in Sanderson et al. U.S. Pat. No. 4,547,598.

Taylor et al. U.S. Pat. No. 4,551,553 is directed to a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

Sanderson et al. disclose the use of a variety of catalysts for the decomposition of tertiary butyl hydroperoxide in a series of U.S. patents, including a catalyst composed of unsupported nickel, copper, chromia and iron (U.S. Pat. No. 4,704,482), a catalyst composed of iron, copper, chromia and cobalt (U.S. Pat. No. 4,705,903), a catalyst composed of a base treated hydrogenation catalyst from groups VIB or VIIIB of the Periodic Table (U.S. Pat. No. 4,742,179), a catalyst consisting essentially of nickel, copper, chromium and barium (U.S. Pat. No. 4,873,380), a catalyst composed of a metal phthalocyanine promoted with a rhenium compound (U.S. Pat. No. 4,910,349), a catalyst composed of a base promoted metal phthalocyanine compound (U.S. Pat. No. 4,912,269), a catalyst composed of a soluble ruthenium compound promoted with a bidentate ligand (U.S. Pat. No. 4,912,033), a catalyst composed of a metal porphine such as iron (III) or manganese (III) promoted with an alkyl thiol or an amine, a catalyst composed of an imidazole promoted metal phthalocyanine compound (U.S. Pat. No. 4,912,266), (U.S. Pat. No. 4,922,034), a catalyst composed of a metal phthalocyanine promoted with a thiol and a free radical inhibitor (U.S. Pat. No. 4,922,035), a catalyst composed of a borate promoted metal phthalocyanine (U.S. Pat. No. 4,922,036), or a catalyst composed of a soluble ruthenium compound and an iron compound such as an acetate, a borate, a bromide, a chloride, a 1,3-propanedionate, a 2-ethyl-hexanoate, an iodide, a nitrate, a 2,4-pentanedionate, a perchlorate or a sulfate (U.S. Pat. No. 5,025,113).

BACKGROUND INFORMATION

When isobutane is reacted with molecular oxygen, the principal products of the reaction are tertiary butyl alcohol and tertiary butyl hydroperoxide. However, minor amounts of other contaminants are also formed.

In addition, a minor amount of water will be formed, which will normally amount to about 0.5 to 1 wt. % of the reactor effluent. The amount of byproduct water that is produced is a function of the severity of the reaction conditions employed and will tend to increase as the severity of the reaction conditions is increased.

As indicated, tertiary butyl hydroperoxide is useful as a raw material for the manufacture of tertiary butyl alcohol. The tertiary butyl alcohol can be formed by catalytic decomposition of the tertiary butyl hydroperoxide. In the Williams et al. process disclosed in U.S. Pat. No. 3,472,876, an oxygen-containing gas was charged to a reactor containing isobutane and an oxidation catalyst to provide a reaction mixture comprising tertiary butyl alcohol, tertiary butyl hydroperoxide, acetone, and tertiary butyl ether. The reported results in the patent indicate that there was a comparatively low rate of conversion and a comparatively poor selectivity of the reaction to tertiary butyl alcohol.

SUMMARY OF THE INVENTION

In accordance with the present invention, a solvent solution of a tertiary butyl hydroperoxide charge stock is brought into contact with a catalytically effective amount of a hydroperoxide decomposition catalyst in a hydroperoxide decomposition reaction zone in liquid phase with agitation to convert the tertiary butyl hydroperoxide to decomposition products, principally tertiary butyl alcohol, the hydroperoxide decomposition catalyst consisting essentially of alumina having from about 0.5 to about 25 wt. % of lead oxide deposited thereon and tertiary butyl alcohol is recovered from the products of the hydroperoxide decomposition reaction.

The tertiary butyl alcohol will not be the only decomposition product that is formed. Minor amounts of other oxygen-containing materials such as those listed above will also be formed.

DESCRIPTION OF THE PROCESS OF THE PRESENT INVENTION

The starting materials for the process of the present invention are a tertiary butyl hydroperoxide feedstock and an alumina supported lead oxide catalyst.

The Tertiary Butyl Hydroperoxide Feedstock

The tertiary butyl hydroperoxide charge stock may comprise an isobutane oxidation product wherein the tertiary butyl hydroperoxide is dissolved in a mixture of isobutane and tertiary butyl alcohol or may comprise an isobutane oxidation product enriched by the addition of tertiary butyl alcohol, such that the solution of tertiary butyl alcohol in the mixture of isobutane with tertiary butyl alcohol contains from about 5 to about 30 wt. % of tertiary butyl hydroperoxide.

Alternately, the isobutane reaction product may be charged to a distillation zone where unreacted isobutane is removed as a distillate fraction for recycle to thereby provide a solution of tertiary butyl hydroperoxide in tertiary butyl alcohol containing about 5 to about 30 wt. % of tertiary butyl hydroperoxide.

The Catalyst System

The hydroperoxide decomposition catalyst to be used in accordance with the present invention is a supported hydroperoxide decomposition catalyst consisting essentially of alumina having from about 0.5 to about 25 wt. % of lead oxide deposited thereon.

Catalytic Decomposition of Tertiary Butyl Hydroperoxide

The process of the present invention may be conducted batchwise in kettles or by continuously passing the reactants through a tubular reactor.

The catalytic decomposition of the tertiary butyl hydroperoxide is preferably conducted at a temperature within the range of about 20° to about 160° C. and, more preferably, at a temperature within the range of about 80° to about 100° C. The reaction is preferably conducted at a pressure sufficient to keep the reactants and the reaction products in liquid phase. A pressure of about 0 to about 10,000 psig. may be used, if desired.

Flow rates of the charge solution to the reaction zone should be adjusted in order to provide an appropriate contact time within the reactor. In a batch process, the holding time may suitably be from about 0.5 to about 10 hours, and more preferably about 1 to 3 hours.

In accordance with a preferred embodiment of the present invention, isobutane is reacted with oxygen in an oxidation zone under oxidation reaction conditions including a temperature of about 135° to about 155° C., a pressure of about 300 to about 800 psig., and a holding time of about 2 to about 6 hours to provide an initial oxidation reaction product comprising unreacted isobutane, tertiary butyl hydroperoxide, tertiary butyl alcohol, and oxygen-containing by-products. The initial oxidation reaction product is then used as the tertiary butyl hydroperoxide charge stock of the present invention. If the concentration of tertiary butyl hydroperoxide in the tertiary butyl hydroperoxide charge stock is more than about 30 wt. % of the initial oxidation reaction product, the initial oxidation reaction product can be diluted with an amount of tertiary butyl alcohol sufficient to lower the concentration of the tertiary butyl hydroperoxide to a desired percentage, to provide, for example, a tertiary butyl hydroperoxide charge stock containing from about 15 to about 25 wt. % of tertiary butyl hydroperoxide.

Alternately, the initial oxidation reaction product may be fractionated in any appropriate manner (e.g., by distillation in a distillation zone) to remove the isobutane therefrom for recycle and to provide a solution of tertiary butyl hydroperoxide and tertiary butyl alcohol which will normally contain from about 5 to about 30 wt. % of tertiary butyl hydroperoxide.

The solution of tertiary butyl hydroperoxide in tertiary butyl alcohol is then charged to a catalytic hydroperoxide decomposition zone where it is brought into contact with an alumina supported lead oxide catalyst to substantially selectively convert the tertiary butyl hydroperoxide to tertiary butyl alcohol with high yields and selectivities.

As indicated, the catalytic decomposition of the tertiary butyl hydroperoxide in the catalytic hydroperoxide decomposition reaction zone may suitably be conducted at a temperature within the range of about 20° to about 160° C., preferably from about 60° to about 120° C., and more preferably from about 80° to 100° C. at autogenous pressure or if desired at a superatmospheric pressure up to 1000 psig. for a contact time within the range of about 0.5 to about 10 hours, and more preferably about 1 to 3 hours.

When the process of the present invention is practiced in a continuous manner by continuously charging the tertiary butyl hydroperoxide charge stock to a reactor containing a fixed bed of pelleted hydroperoxide decomposition catalyst, the space velocity is suitably in the range of about 0.5 to about 3 volumes of tertiary butyl hydroperoxide charge stock per volume of catalyst per hour. Preferably, the space velocity is within the range of about 1 to about 32 volumes of tertiary butyl hydroperoxide charge stock per volume of catalyst per hour.

The reaction product from the tertiary butyl hydroperoxide decomposition step may then be fractionated in any suitable manner, such as by distillation to recover the tertiary butyl alcohol.

SPECIFIC EXAMPLES

The invention will be further illustrated by the following specific examples which are given by way of illustration and not as limitations on the scope of this invention.

Procedure

The reactor that was used for the experiments was a stainless steel tube (0.51"×29") which was electrically heated. Liquid feed was pumped into the bottom of the reactor using a Ruska dual drive pump. Pressure was regulated using a Skinner Uni-Flow valve and a Foxboro controller. Samples were collected at the top of the reactor, cooled to ambient temperature, filtered and analyzed by GC. The analysis of the feed and of the products obtained is reported in the following tables.

Example 1

In this example, the catalyst consisted essentially of lead oxide supported on alumina.

TABLE 1

CATALYTIC CONVERSION OF TERT-BUTYLHYDROPEROXIDE TO TERT-BUTYLALCOHOL

| Notebook Number | 6844-10-A | 6906-34-1 | 6906-34-2 | 6906-34-3 | 6906-34-4 |
|---|---|---|---|---|---|
| Catalyst |  | PbO on $Al_2O_3$ | PbO on $Al_2O_3$ | PbO on $Al_2O_3$ | PbO on $Al_2O_3$ |
| Catalyst (cc) |  | 100 | 100 | 100 | 100 |
| Pressure (psig) |  | 500 | 500 | 500 | 500 |
| Feed Rate (cc/Hr.) |  | 50 | 50 | 50 | 50 |
| Temperature (°C.) |  | 80 | 100 | 120 | 140 |
| Time on Stream (Hr) |  | 4 | 4 | 4 | 4 |
| Space Vel. (cc/cc) |  | 0.5 | 0.5 | 0.5 | 0.5 |
| TBHP Conversion (mol. %) |  | 72.5 | 82.1 | 95.0 | 98.3 |
| Selectivity IC4= (mol. %) |  | −0.0 | 0.0 | −0.0 | 0.0 |
| Sel. Acetone (mol. %) |  | 8.5 | 14.0 | 18.7 | 27.9 |
| Sel. Methanol (mol. %) |  | 1.4 | 2.6 | 5.0 | 8.0 |
| Sel. TBA (mol. %) |  | 83.9 | 80.3 | 78.1 | 70.9 |
| Sel. DTBP (mol. %) |  | 7.7 | 5.7 | 3.2 | 1.3 |
| Remarks | $H_2O$ Free Basis | $H_2O$ Free Basis | $H_2O$ Free Basis | $H_2O$ Free Basis | $H_2O$ Free Basis |
| Composition, wt % |  |  |  |  |  |
| IC4= | 0.001 | 0.000 | 0.001 | 0.000 | 0.002 |
| MEOH/MF | 0.016 | 0.083 | 0.162 | 0.337 | 0.552 |
| Acetone | 0.008 | 0.765 | 1.429 | 2.206 | 3.385 |
| TBA | 79.968 | 92.463 | 93.740 | 95.496 | 95.005 |
| DTBP | 0.055 | 0.917 | 0.785 | 0.521 | 0.251 |
| TBHP | 19.146 | 5.270 | 3.419 | 0.948 | 0.333 |

TABLE 2

CATALYTIC CONVERSION OF TERT-BUTYLHYDROPEROXIDE TO TERT-BUTYLALCOHOL

| Notebook Number | 6844-10-A | 6906-35-1 | 6906-35-2 | 6906-35-3 | 6906-35-4 |
|---|---|---|---|---|---|
| Catalyst |  | PbO on $Al_2O_3$ | PbO on $Al_2O_3$ | PbO on $Al_2O_3$ | PbO on $Al_2O_3$ |
| Catalyst (cc) |  | 100 | 100 | 100 | 100 |
| Pressure (psig) |  | 500 | 500 | 500 | 500 |
| Feed Rate (cc/Hr.) |  | 100 | 100 | 100 | 100 |
| Temperature (°C.) |  | 80 | 100 | 120 | 140 |
| Time on Stream (Hr) |  | 4 | 4 | 4 | 4 |
| Space Vel. (cc/cc) |  | 1.0 | 1.0 | 1.0 | 1.0 |
| TBHP Conversion (mol. %) |  | 15.3 | 40.8 | 83.4 | 97.3 |
| Selectivity IC4= (mol. %) |  | −0.1 | −0.0 | −0.0 | 0.0 |
| Sel. Acetone (mol. %) |  | 11.1 | 12.0 | 18.1 | 35.5 |
| Sel. Methanol (mol. %) |  | 1.9 | 2.6 | 5.8 | 10.5 |
| Sel. TBA (mol. %) |  | 80.9 | 82.0 | 79.2 | 64.0 |
| Sel. DTBP (mol. %) |  | 8.0 | 6.0 | 2.7 | 0.5 |
| Remarks | $H_2O$ Free Basis | $H_2O$ Free Basis | $H_2O$ Free Basis | $H_2O$ Free Basis | $H_2O$ Free Basis |
| Composition, wt % |  |  |  |  |  |
| IC4= | 0.001 | 0.000 | 0.000 | 0.000 | 0.004 |
| MEOH/MF | 0.016 | 0.036 | 0.088 | 0.343 | 0.713 |
| Acetone | 0.008 | 0.216 | 0.612 | 1.872 | 4.275 |
| TBA | 79.968 | 82.443 | 86.692 | 93.593 | 93.536 |

TABLE 2-continued
CATALYTIC CONVERSION OF TERT-BUTYLHYDROPEROXIDE TO TERT-BUTYLALCOHOL

| Notebook Number | 6844-10-A | 6906-35-1 | 6906-35-2 | 6906-35-3 | 6906-35-4 |
|---|---|---|---|---|---|
| DTBP | 0.055 | 0.245 | 0.438 | 0.401 | 0.127 |
| TBHP | 19.146 | 16.226 | 11.335 | 3.176 | 0.518 |

TABLE 3
CATALYTIC CONVERSION OF TERT-BUTYLHYDROPEROXIDE TO TERT-BUTYLALCOHOL

| Notebook Number | 6844-10-A | 6906-36-1 | 6906-36-2 | 6906-36-3 | 6906-36-4 |
|---|---|---|---|---|---|
| Catalyst | | PbO on $Al_2O_3$ | PbO on $Al_2O_3$ | PbO on $Al_2O_3$ | PbO on $Al_2O_3$ |
| Catalyst (cc) | | 100 | 100 | 100 | 100 |
| Pressure (psig) | | 500 | 500 | 500 | 500 |
| Feed Rate (cc/Hr.) | | 200 | 200 | 200 | 200 |
| Temperature (°C.) | | 80 | 100 | 120 | 140 |
| Time on Stream (Hr) | | 4 | 4 | 4 | 4 |
| Space Vel. (cc/cc) | | 2.0 | 2.0 | 2.0 | 2.0 |
| TBHP Conversion (mol. %) | | 2.4 | 30.5 | 77.3 | 92.3 |
| Selectivity IC4= (mol. %) | | 0.0 | −0.0 | 0.0 | −0.0 |
| Sel. Acetone (mol. %) | | 0.0 | 12.7 | 20.1 | 29.8 |
| Sel. Methanol (mol. %) | | 0.0 | 2.5 | 6.0 | 11.0 |
| Sel. TBA (mol. %) | | 0.0 | 82.5 | 77.2 | 69.3 |
| Sel. DTBP (mol. %) | | 0.0 | 4.8 | 2.7 | 0.9 |
| Remarks | $H_2O$ Free Basis | $H_2O$ Free Basis | $H_2O$ Free Basis | $H_2O$ Free Basis | $H_2O$ Free Basis |
| Composition, wt % | | | | | |
| IC4= | 0.001 | 0.000 | 0.000 | 0.001 | 0.000 |
| MEOH/MF | 0.016 | 0.021 | 0.068 | 0.333 | 0.708 |
| Acetone | 0.008 | 0.065 | 0.488 | 1.926 | 3.398 |
| TBA | 79.968 | 80.073 | 84.992 | 92.240 | 93.509 |
| DTBP | 0.055 | 0.129 | 0.281 | 0.379 | 0.191 |
| TBHP | 19.146 | 18.687 | 13.297 | 4.354 | 1.474 |

A 19.1% solution of TBHP in TBA was converted in good yield to TBA over a heterogenous lead oxide on alumina catalyst. For example, at 80° C. using a 100 cc reactor and a space velocity of 0.5, a 72.5% conversion of TBHP was obtained with the following selectivities: TBA 83.9%; DTBP 7.7%; acetone 8.5%; methanol 1.4%.

Having thus described our invention, what is claimed is:

1. In a method wherein a solvent solution of a tertiary butyl hydroperoxide charge stock is brought into contact with a catalytically effective amount of a hydroperoxide decomposition catalyst in a hydroperoxide decomposition reaction zone in liquid phase with agitation to convert said tertiary butyl hydroperoxide to decomposition products, principally tertiary butyl alcohol, the improvement which comprises:
   a) using, as said hydroperoxide decomposition catalyst, a supported hydroperoxide decomposition catalyst consisting essentially of lead oxide supported on alumina, and
   b) recovering tertiary butyl alcohol from the products of said hydroperoxide decomposition reaction.

2. A method as in claim 1 wherein the solvent comprises tertiary butyl alcohol.

3. A method as in claim 1 wherein the solvent comprises a mixture of isobutane with tertiary butyl alcohol.

4. In a method wherein a solution of a tertiary butyl hydroperoxide charge stock in tertiary butyl alcohol that contains from about 5 to about 30 wt. % of tertiary butyl hydroperoxide is brought into contact with a catalytically effective amount of a hydroperoxide decomposition catalyst in a hydroperoxide decomposition reaction zone in liquid phase with agitation under hydroperoxide conversion conditions including a temperature within the range of about 25° to about 250° C. and a pressure of about 0 to about 1,000 psig to convert said tertiary butyl hydroperoxide to decomposition products, principally tertiary butyl alcohol, the improvement which comprises:
   a) using, as said hydroperoxide decomposition catalyst, a supported hydroperoxide decomposition catalyst consisting essentially of alumina having deposited thereon from about 0.5 to about 25 wt. % of lead oxide, and
   b) recovering tertiary butyl alcohol from the products of said hydroperoxide decomposition reaction.

5. A method as in claim 4 wherein the temperature is in the range of about 40° to about 150° C. and the pressure is about 0 psig.

6. In a method wherein a solution of a tertiary butyl hydroperoxide charge stock in a mixture of isobutane with tertiary butyl alcohol that contains from about 5 to about 30 wt. % of tertiary butyl hydroperoxide is brought into contact with a catalytically effective amount of a hydroperoxide decomposition catalyst in a hydroperoxide decomposition reaction zone in liquid phase under hydro- peroxide conversion conditions including a temperature within the range of about 25° to about 250° C. and a pressure of about 0 to about 10,000 psig to convert said tertiary butyl hydroperoxide to decomposition products, principally tertiary butyl alcohol, the improvement which comprises:
   a) using, as said hydroperoxide decomposition catalyst, a decomposition catalyst consisting essentially of alumina having deposited thereon from about 0.5 to about 25 wt. % of lead oxide, and
   b) recovering tertiary butyl alcohol from the products of said hydroperoxide decomposition reaction.

7. A method as in claim 6 wherein the temperature is in the range of about 40° to about 150° C. and the pressure is about 0 psig.

* * * * *